(12) United States Patent
McPeek

(10) Patent No.: US 10,539,545 B2
(45) Date of Patent: *Jan. 21, 2020

(54) SYSTEMS AND METHODS FOR MONITORING AGRICULTURAL PRODUCTS

(71) Applicant: AGERpoint, Inc., New Smyrna Beach, FL (US)

(72) Inventor: K. Thomas McPeek, Orlando, FL (US)

(73) Assignee: AGERPOINT, INC., New Smyrna Beach, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 16/518,148

(22) Filed: Jul. 22, 2019

(65) Prior Publication Data
US 2019/0339243 A1    Nov. 7, 2019

Related U.S. Application Data

(63) Continuation of application No. 15/868,840, filed on Jan. 11, 2018, now Pat. No. 10,371,683, which is a continuation of application No. 13/907,147, filed on May 31, 2013, now Pat. No. 9,939,417.

(60) Provisional application No. 61/654,312, filed on Jun. 1, 2012.

(51) Int. Cl.
*G01N 33/00* (2006.01)
*G01N 21/25* (2006.01)
*G01N 33/02* (2006.01)
*G01B 5/00* (2006.01)
*G01B 11/24* (2006.01)
*G01N 21/84* (2006.01)
*G01N 21/17* (2006.01)

(52) U.S. Cl.
CPC ....... *G01N 33/0098* (2013.01); *G01B 5/0035* (2013.01); *G01N 21/251* (2013.01); *G01N 33/025* (2013.01); *G01B 11/24* (2013.01); *G01N 2021/1797* (2013.01); *G01N 2021/8466* (2013.01)

(58) Field of Classification Search
CPC ............ G01N 33/0098; G01N 21/251; G01N 2021/1797; G01N 2021/8466; G01B 5/0035; G01B 11/24
See application file for complete search history.

(56) References Cited

U.S. PATENT DOCUMENTS 6,862,083 B1 * 3/2005 McConnell, Sr. ... A01B 79/005
356/4.01

* cited by examiner

*Primary Examiner* — Yoshihisa Ishizuka
(74) *Attorney, Agent, or Firm* — Bryan Cave Leighton Paisner LLP

(57) ABSTRACT

The present invention relates to systems and methods for monitoring agricultural products. In particular, the present invention relates to monitoring fruit production, plant growth, and plant vitality.

16 Claims, 5 Drawing Sheets

Figure 2

| TASK TYPE 1 | Determine diameter and/or circumference of the trunk of each tree<br>Determine the overall height of each tree<br>Determine the overall volume of each tree<br>Determine the leaf density of each tree<br>Determine average leaf color of each tree | TOOL 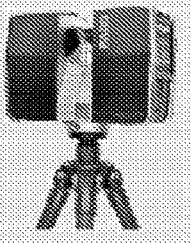 |
|---|---|---|
| TASK TYPE 2 | Determine the GPS location of each tree<br>Attach a unique RFID - Barcode identifier to each tree | TOOL  |
| TASK TYPE 3 | Determine the predicted yield from blossom and fruit | TOOL 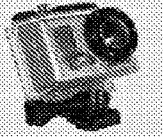 |
| TASK TYPE 4 | Seamlessly connect to existing industry standard software solutions for tracking grove operations and harvest control | TOOL 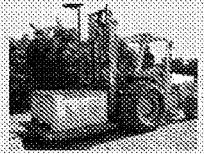 |

SYSTEMS AND METHODS FOR MONITORING AGRICULTURAL PRODUCTS

CROSS REFERENCE TO RELATED APPLICATIONS

This application is continuation application of U.S. application Ser. No. 15/868,840, filed Jan. 11, 2018, which is a continuation of U.S. application Ser. No. 13/907,147, filed May 31, 2013, now U.S. Pat. No. 9,939,417, which claims priority to U.S. Provisional Patent Application No. 61/654,312, filed Jun. 1, 2012. The entire contents of the above applications are incorporated by reference as if recited in full herein.

FIELD OF THE INVENTION

The present invention relates to systems and methods for monitoring agricultural products. In particular, the present invention relates to monitoring fruit production, plant growth, and plant vitality.

BACKGROUND OF THE INVENTION

Accurate and timely machine counting of fruit on the tree or vine has long been considered impossible or impractical. Current methods rely on manual estimation and are often inaccurate and labor intensive. Inaccurate estimates lead to inaccurate crop forecasts and complicate pricing and grower's ability to forecast and plan.

What is needed is an improved method for accurately forecasting crop size and quality.

SUMMARY OF THE INVENTION

The present invention relates to systems and methods for monitoring agricultural products. In particular, the present invention relates to monitoring fruit production, plant growth, and plant vitality.

Embodiments of the present disclosure provide systems and methods for improved fruit tree analysis and crop predictions. The systems and methods described herein improve on the accuracy and efficiency of existing methods. The systems and methods of embodiments of the present invention find use in research and commercial agriculture, among other uses.

For example, in some embodiments, the present invention provides an analysis system, comprising: a) a data acquisition component; b) optionally, a transport component configured to transport the data acquisition component to collect data on fruit trees or vines; and c) a software component configured to analyze the data to generate analyzed data. In some embodiments, the data acquisition component comprises one or more devices selected from, for example, one or more of a 3D laser scanner, a survey grade GPS, thermal imaging, radio, sound and magnetic waves, a thermal imaging camera, multispectral and/or hyperspectral sensors, or a high speed high density (HD) video camera. In some embodiments, the data, for example, one or more of tree trunk diameter, height of tree, volume of tree, leaf density of tree, color of leaves on tree, GPS location of tree, bar code data for tree, number of blossoms on tree, presence of disease on said fruit or tree, subspecies of said tree, or an annotated or un-annotated photograph of said tree. The present invention is not limited to the analysis of a particular fruit tree or vine. Examples include but are not limited to, abiu, accrola, almond, amla (indian gooseberry), apple, apricot, aprium, avocados, bael, bananas, ber (indian plum), blackberries, blood orange, blueberries, breadfruit, calamondin, cantaloupe melon, carambola (starfruit), cashew, the fruit, cherries, chestnut, chocolate, chokecherry, citron, coconuts, coffee, corn plant, crabapple, cumaquat, currant, custard-apple, dates, dewberries, dragon fruit, durian, feijoa, fig, grapefruit, grapes, guava, hazelnut, honeydew, hops, jaboticaba, jackfruit, jujube, kaffir lime, key lime, kiwifruit, kumquat, lemons, limes, loganberries, longan, loquat, lychee, mandarin, mangoes, mangosteen, medlar, morello cherry, mulberries, natal plum, nectarines, olives, oranges, papayas, passion fruit, pawpaw, peaches, pears, pecan, persimmon, pineapples, plums, pluot, pomegranate, pomclo, prune, pummel, pumpkin, raspberries, red banana, rock melon, sabinc, sapodilla (chikoo), sapote, soursop, starfruit, stone fruit, strawberries, strawberry tree, sugar-apple (sharifa), surinam cherry, tamarillo, tamarind, tangelos, tangerines, tomatoes, ugli, uglifruit/uniqfruit, walnut, watermelon, a grape vine, a tomato vine, a corn plant or an apple tree. In some embodiments, the software component further comprises a computer processor and a user interface configured to provide or display the analyzed data (e.g., to a user). In some embodiments, the analyzed data is, for example, one or more of tree health, predicted fruit yield, or predicted fruit ripening period.

In further embodiments, the present invention provides a method, comprising: a) collecting data on plants (e.g., fruit trees) using a data acquisition component transported by a transport component; and b) analyzing the data with a software component to generate analyzed data. In some embodiments, the method further comprises the step of using the analyzed data to guide fruit tree sprayers (e.g., to determine when to spray, how long to spray, and what chemicals to spray). In some embodiments, the method further comprises the step of identifying species and/or subspecies of the tree. In some embodiments, the method further comprises the step of identifying disease in the tree and/or fruit.

Additional embodiments are described herein.

DESCRIPTION OF THE FIGURES

FIG. 2 shows a task—methodology breakdown of systems and methods of embodiments of the present invention.

DEFINITIONS

Figure 1:
FIG. 1 shows an image of annotations of trees generated by systems and methods of embodiments of the present invention.
Figure 3:
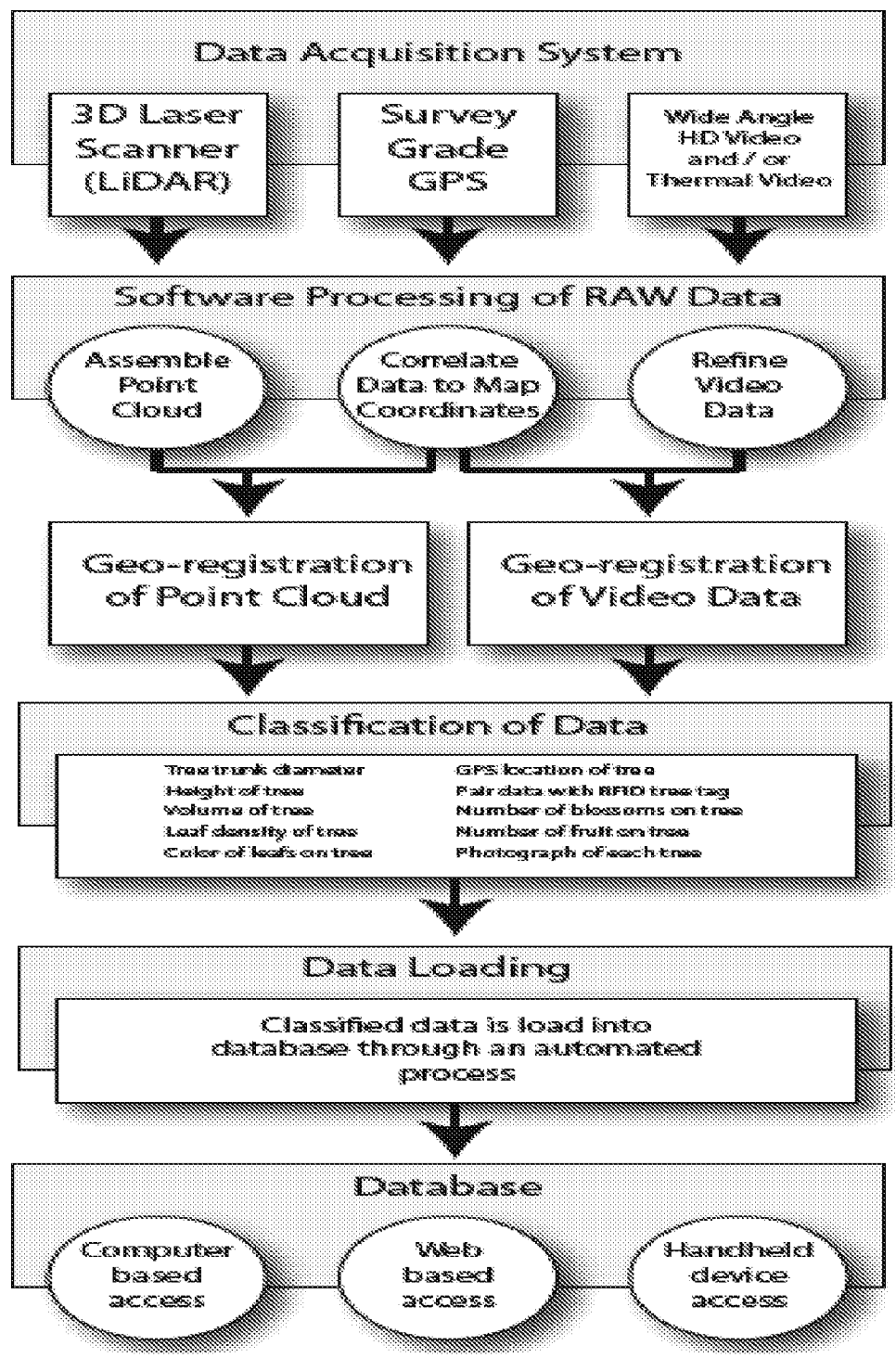
FIG. 3 shows a schematic of an exemplary crop analysis system for fruit bearing trees and vine crops.
Figure 4:
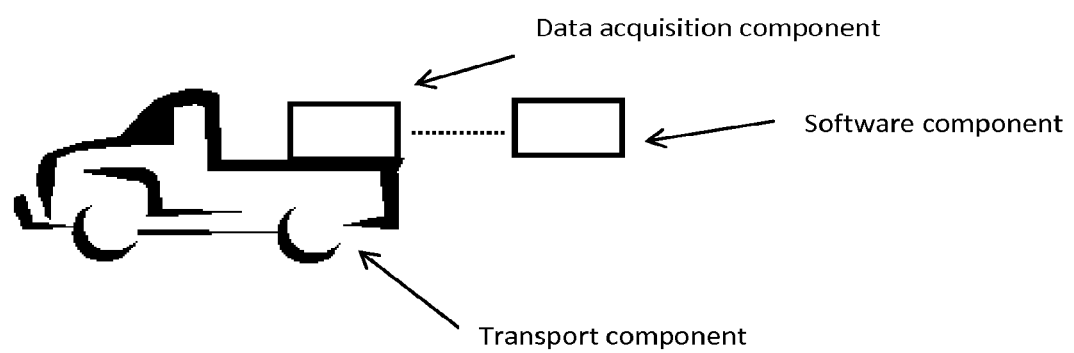
FIG. 4 shows a schematic of an exemplary crop analysis system for fruit bearing trees and vine crops.

To facilitate understanding of the invention, a number of terms are defined below.

As used herein, the terms "processor" and "central processing unit" or "CPU" are used interchangeably and refer to a device that is able to read a program from a computer memory (e.g., ROM or other computer memory) and perform a set of steps according to the program.

As used herein, the terms "computer memory" and "computer memory device" refer to any storage media readable by a computer processor. Examples of computer memory include, but are not limited to, RAM, ROM, computer chips, digital video discs (DVD), compact discs (CDs), hard disk drives (HDD), and magnetic tape.

As used herein, the term "computer readable medium" refers to any device or system for storing and providing information (e.g., data and instructions) to a computer processor. Examples of computer readable media include, but are not limited to, DVDs, CDs, hard disk drives, magnetic tape and servers for streaming media over networks.

As used herein, the term "in electronic communication" refers to electrical devices (e.g., computers, processors, etc.) that are configured to communicate with one another through direct or indirect signaling.

As used herein, the term "survey grade GPS" refers to global positioning satellite (GPS) receivers that are able to map locations with a very high degree of accuracy. For example, in some embodiments, survey grade GPS receivers are accurate below 1 centimeter (0.4 inches) or lower.

As used herein, the term "fruit tree" refers to any woody tree or vine that produces a fruit. The term "fruit" refers to a part of a flowering plant that derives from specific tissues of the flower and is not limited to culinary fruits. Examples include but are not limited to, abiu, acerola, almond, amla (indian gooseberry), apple, apricot, aprium, avocados, bael, bananas, ber (indian plum), blackberries, blood orange, blueberries, breadfruit, calamondin, cantaloupe melon, carambola (starfruit), cashew, the fruit, cherries, chestnut, chocolate, chokecherry, citron, coconuts, coffee, corn plant, crabapple, cumaquat, currant, custard-apple, dates, dewberries, dragon fruit, durian, feijoa, fig, grapefruit, grapes, guava, hazelnut, honeydew, hops, jaboticaba, jackfruit, jujube, kaffir lime, key lime, kiwifruit, kumquat, lemons, limes, loganberries, longan, loquat, lychee, mandarin, mangoes, mangosteen, medlar, morello cherry, mulberries, natal plum, nectarines, olives, oranges, papayas, passion fruit, pawpaw, peaches, pears, pecan, persimmon, pineapples, plums, pluot, pomegranate, pomelo, prune, pummel, pumpkin, raspberries, red banana, rock melon, sabine, sapodilla (chikoo), sapote, soursop, starfruit, stone fruit, strawberries, strawberry tree, sugar-apple (sharifa), surinam cherry, tamarillo, tamarind, tangelos, tangerines, tomatoes, ugli, uglifruit/uniqfruit, walnut, watermelon, a grape vine, a tomato vine, a corn plant or an apple tree. In some embodiments, the fruit tree is a citrus tree (e.g., those described above).

DETAILED DESCRIPTION OF THE INVENTION

The present invention relates to systems and methods for monitoring agricultural products. In particular, the present invention relates to monitoring fruit production and plant growth.

The ability to accurately predict fruit yield and quality in advance of harvest provides a significant advancement in the fruit growing industry. The systems and methods of embodiments of the present invention provide an accurate inventory of crop holdings, including images and geo-location of each plant, as well as providing point cloud data dissemination.

Embodiments of the present invention provide systems and methods for assessing agricultural crops (e.g., fruit trees or vines). The systems and methods described herein find use in a variety of applications (e.g., providing information to companies engaged in growing fruit crops, those insuring fruit crops and those who invest in agricultural commodities).

The present invention is not limited to a particular fruit tree or vine. Any fruit bearing plant may be analyzed using the systems and methods described herein. Examples include but are not limited to abiu, acerola, almond, amla (indian gooseberry), apple, apricot, aprium, avocados, bael, bananas, ber (indian plum), blackberries, blood orange, blueberries, breadfruit, calamondin, cantaloupe melon, carambola (starfruit), cashew, the fruit, cherries, chestnut, chocolate, chokecherry, citron, coconuts, coffee, corn plant, crabapple, cumaquat, currant, custard-apple, dates, dewberries, dragon fruit, durian, feijoa, fig, grapefruit, grapes, guava, hazelnut, honeydew, hops, jaboticaba, jackfruit, jujube, kaffir lime, key lime, kiwifruit, kumquat, lemons, limes, loganberries, longan, loquat, lychee, mandarin, mangoes, mangosteen, medlar, morello cherry, mulberries, natal plum, nectarines, olives, oranges, papayas, passion fruit, pawpaw, peaches, pears, pecan, persimmon, pineapples, plums, pluot, pomegranate, pomelo, prune, pummel, pumpkin, raspberries, red banana, rock melon, sabine, sapodilla (chikoo), sapote, soursop, starfruit, stone fruit, strawberries, strawberry tree, sugar-apple (sharifa), surinam cherry, tamarillo, tamarind, tangelos, tangerines, tomatoes, ugli, uglifruit/uniqfruit, walnut, watermelon, a grape vine, a tomato vine, a corn plant or an apple tree. In some embodiments, the fruit tree is a citrus tree (e.g., those described above).

In some embodiments, the present invention provides systems and methods for a) determining the diameter and/or circumference of a tree trunk or vine stem, determining the overall height of each tree or vine, determining the overall volume of each tree or vine, determining the leaf density and average leaf color of each tree or vine; b) determining the GPS location of each plant and attaches a unique identifier (e.g., RFID (e.g., barcode identifier)) to each plant or vine; c) determining the predicted yield from identified blossom and fruit; and d) providing yield and harvest date predictions or other information to end users using a user interface. In some embodiments, the technology is used to size fruit while it is still on the tree (e.g., for applications where selective harvest is done based on size).

Embodiments of the present invention provide a variety of hardware and software systems to perform the described methods. In some embodiments, systems comprise one or more (e.g., all) the following components: survey grade GPS, 3D laser scanners, static and motion imaging (e.g., RGB, multi-spectral, hyper-spectral, NWIR and SWIR), high speed HD video, transport vehicles, computer software, computer processors, and user interfaces.

The Global Positioning System (GPS) is a space-based satellite navigation system that provides location and time information in all weather, anywhere on or near the Earth, where there is an unobstructed line of sight to four or more GPS satellites. GPS systems generally fall in one of four categories of accuracy, Sub Centimeter (0.39370 inch), Sub Decimeter (3.937 inches), Sub Meter (39.37 inches), and Sub Decameter (32.8 Feet). In some embodiments, survey grade GPS (e.g., sub centimeter) is used to locate fruit, and trees or vines to high levels of detail. Survey grade GPS receivers determine location to very high accuracy (e.g., 1 inch or less, 1 centimeter or less, etc.).

In some embodiments, commercially available equipment is utilized. For example, survey grade GPS receivers are available from a variety of suppliers (e.g., Igage Mapping Corporation, Salt Lake City, Utah; Hemisphere Inc., Calgary, Alberta, Canada; Trimble Navigation Limited, Sunnyvale, Calif.).

Figure 5:
FIG. 5 shows an example of a point cloud map of a fruit tree.

In some embodiments, 3D laser scanners are utilized to map fruit or tree or vine properties. 3D scanner is a colloquial term used to describe a device used for Light Detection and Ranging (LiDAR) which is an optical remote sensing technology that can measure the distance to, or other properties of a target by illuminating the target with light. LiDAR can be found in two common forms direct energy detection, also known as incoherent, and coherent detection. Coherent systems are typically preferred for measurement systems. Both systems are currently available in two pulse formats: micropulse and high-energy systems. The micropulse systems are eyesafe and require less energy to operate but this comes at the expense of higher computational post-processing requirements. LiDAR systems currently in use are capable of collecting nearly one million points per second. The data collected is represented as a point cloud as demonstrated in FIG. 5. 3D laser scanners are commercially available (e.g., from Tiger Supplies Inc., Irvington N.J.; Laser Design and GKS Services, Minneapolis, Minn.; Riegl USA, Orlando, Fla. and Faro USA, Lake Mary, Fla.). In some embodiments, waveform LiDAR (e.g., available from Riegl, Orlando, Fla.) is utilized.

In some embodiments, high speed high density (HD) video is used to capture images of fruits and tree or vine features. The quality of video captured is important for accurate analysis. In some embodiments, video that is uncompressed 1080p at a speed of 60 frames a second or faster is utilized. In some embodiments, a fisheye lenses of 160° or greater is utilized.

Infrared thermography (IRT), thermal imaging, and thermal video are examples of infrared imaging science. Thermal imaging cameras detect radiation in the infrared range of the electromagnetic spectrum (roughly 9,000-14,000 nanometers or 9-14 μm) and produce images of that radiation, called thermograms. Since infrared radiation is emitted by all objects above absolute zero according to the black body radiation law, thermography makes it possible to see one's environment with or without visible illumination. The amount of radiation emitted by an object increases with temperature; therefore, thermography allows one to see variations in temperature. This is particularly useful when dealing with plant species that have very dense leaf coverage since the temperature differential between the leaf and the fruit are very different temperature profiles. High speed HD video hardware is commercially available (e.g., from NAC Image Technology, Simi Valley, Calif.; Olympus, Tokyo, Japan; Panasonic). Thermal imaging equipment is commercially available (e.g., from FLIR Systems, Boston, Mass. and L-3 Communications, New York, N.Y.).

In some embodiments, the capturing of this data utilizes specialized equipment mounted to vehicle (e.g., 4 wheel drive, flying vehicle, or off road vehicle). Any manned or unmanned vehicle that drives on the ground or flies low to the ground (e.g., unmanned or manned aircraft) may be utilized to transport the mapping hardware throughout the area to be surveyed. In some embodiments, a single data collection unit is capable of scanning two acres or more (e.g., 5, 10, 12, 15 or more) per hour in terrestrial applications.

In some embodiments, the present invention provides data analysis software and computer hardware configured to analyze data from the GPS, scanners and video cameras described herein. In some embodiments, analysis systems include user interfaces and display systems. For example, the 3D scanner creates a point cloud which is a set of vertices in a three-dimensional coordinate system. These vertices are usually defined by X, Y, and Z coordinates, and is typically intended to be representative of the external surface of an object. In some embodiments, point clouds of trees and vines are collected to determine the height of the plant, the trunk diameter, and the leaf density, all of which are determinants of health and productivity and each of these is derived as part of an automated process called classification. The classified data is then loaded, another automated process, into the database for access by the end user.

In some embodiments, software analyzes imaging data on a per tree or per vine basis. In some embodiments, data collected for a particular tree or orchard is inserted into a relational database providing connectivity to other industry standard software products. In some embodiments, software performs one or more (e.g., all) of the following functions: a) assembly of point cloud; b) correlation of data to map coordinates; c) refining of video data; and d) geo-registration of point cloud and video data. In some embodiments, the following information is provided to an end user: tree trunk diameter, height of tree, volume of tree, leaf density of tree, color of leaves on tree, GPS location of tree, bar code data for tree, number of blossoms on tree, and an annotated or un-annotated photograph of the tree (see e.g., FIG. 1).

In some embodiments, the present invention provides methods of analyzing fruit free quality and growth (e.g., including but not limited to, counting blossoms or fruit on the tree or vine (green or ripe), geo-locating plant or trees, determining age and health of tree or vine based on trunk diameter, leaf density, leaf color and overall volume). The methods find use in a variety of research and commercial applications in the agricultural, finance, banking, commodities, property appraisal, and insurance industry.

In some embodiments, crop data is utilized to a allow user to predict crop harvest by counting hanging fruit and measuring trunk diameter, leaf density, leaf color and overall volume. This is accomplished by utilizing a process that collects data in three formats: point cloud via 3D laser scanning; geo-location data via survey grade GPS; and photographic data via High speed HD video and/or thermal imaging.

In some embodiments, the systems and methods described herein find use in identifying subspecies of a particular species of tree or vine. In some embodiments, the systems and methods described herein find use in detecting disease (e.g., through the addition of multispectral and/or hyperspectral sensors). Hyperspectral imaging works by the development of a digital fingerprint. Unlike a conventional digital camera, which has three bands (red, green, blue) multispectral and hyperspectral imaging use more bands. In the case of multispectral dozens and hundreds for hyperspectral. For example, there are approximately 250 species of pecans in the US and the pecan tree has a particular signature in the electromagnetic spectrum and each of those sub-species have related but unique signature. In the case of Disease such as "Citrus Greening", "Blight" or "Citrus Canker" specific conditions are manifested in the leaf, trunk and/or fruit that change the spectral signature making them identifiable through machine vision techniques. Additional details are described, for example, in Lan et al., Applied Engineering in Agriculture Vol. 25(4): 607-615 and Kumar et al., 2010; each of which is herein incorporated by reference in its entirety.

In some embodiments, identification of subspecies or disease is performed simultaneously with the other data that is being collected (LiDAR, photos, etc.) and geo-registered via GPS along with the other data.

In some embodiments, the data collected using the systems and methods described herein finds use in guiding sprayers through real-time mapping or premapping (e.g., commercial sprayers). Spraying represents a very large part of the budget of a grower and using the right kind of spray (herbicide, pesticide, and/or nutrient), in the proper amount, at the right time can have a dramatic impact on the farmers profitability. In some embodiments, data is collected using the systems and methods described herein (e.g., trunk centroid, tree height, canopy density, canopy diameter, species of tree, longitude and latitude) are used to control the sprayers. This data (e.g., in csv format) tells the sprayer as it travels through the grove from precalculated data, on a per tree bases, when to spray, how long to spray, and what chemicals to spray.

In some embodiments, the present invention provides computer implemented systems and methods for performing fruit tree analysis and displaying the results to a user. In some embodiments, computer implemented systems and methods generate a report of the results of the analysis methods that provide information (e.g., fruit yield, tree quality, harvest date predictions, sprayer coordinates) to a user. In some embodiments, the report is provided over the Internet (e.g., on a smart phone, tablet or other wireless communication device) or on a computer monitor.

In some embodiments, the systems and methods of the present invention are provided as an application service provider (ASP) (e.g., can be accessed by users within a web-based platform via a web browser across the Internet; is bundled into a network-type appliance and run within an institution or an intranet; or is provided as a software package and used as a stand-alone system on a single computer).

All publications, patents, patent applications and accession numbers mentioned in the above specification are herein incorporated by reference in their entirety. Although the invention has been described in connection with specific embodiments, it should be understood that the invention as claimed should not be unduly limited to such specific embodiments. Indeed, various modifications and variations of the described compositions and methods of the invention will be apparent to those of ordinary skill in the art and are intended to be within the scope of the following claims.

I claim:

1. A non-transitory computer-readable medium having instructions stored thereon that are executed by a processor to perform operations comprising:
    assembling point cloud data for a plant with a laser scanner in three dimensions to create a plurality of three dimensional vertices having three dimensional coordinates;
    generating photographic data for the plant with a camera to create an image;
    providing a location of a transport vehicle with a global positioning satellite ("GPS") receiver;
    geo-registering the assembled point cloud data such that each three dimensional vertex of the assembled point cloud data is associated with a GPS coordinate based on the location of the transport vehicle;
    geo-registering the photographic data such that each three dimensional vertex of the assembled point cloud data is associated with a pixel of the photographic data;
    providing a color of the plant based on the photographic data of the plant;
    providing classification data of the plant comprising stem diameter, height, volume, and leaf density, wherein the classification data is determined using the GPS coordinates of the assembled point cloud data;
    providing plant quality based on the color of the plant and one of the plant's stem diameter, height, volume, and leaf density; and
    providing instructions to control a fruit tree sprayer to spray the plant, wherein the instructions control when the fruit tree sprayer sprays, how long the fruit tree sprayer sprays, and what chemicals the fruit tree sprayer sprays on the plant based on the quality of the plant.

2. The non-transitory computer-readable medium of claim 1, further comprising providing thermal data from a thermal imaging camera and further determining plant quality based on the thermal data.

3. The non-transitory computer-readable medium of claim 1, wherein the plant quality is based on a blossom count, wherein the blossom count is determined by the geo-registered vertices of the assembled point cloud data.

4. The non-transitory computer-readable medium of claim 1, further comprising providing the point cloud data on a user interface.

5. The non-transitory computer-readable medium of claim 1, further comprising providing plant health based on the geo-registered vertices of the assembled point cloud data.

6. The non-transitory computer-readable medium of claim 1, further comprising guiding the fruit tree sprayer.

7. The non-transitory computer-readable medium of claim 1, further comprising providing spectral data for the plant.

8. The non-transitory computer-readable medium of claim 1, further comprising providing species data of the plant.

9. The non-transitory computer-readable medium of claim 1, further comprising correlating spectral data of the plant with spectral signatures of plant diseases to provide plant disease data of the plant.

10. The non-transitory computer-readable medium of claim 1 further comprising identifying a unique radio frequency identifier ("RFID") code associated with the plant.

11. A plant analyzer comprising:
    a means for assembling point cloud data of a plant by creating a plurality of three dimensional vertices having three dimensional coordinates;
    a means for collecting photographic data of the plant by taking an image of the plant;
    a means for measuring a location of a transport vehicle;
    a server configured to receive the assembled point cloud data, the photographic data, and the location of the transport vehicle; and
    a processor configured to:
        geo-register the assembled point cloud data by associating each three dimensional vertex of the assembled point cloud data with a GPS coordinate based on the location of the transport vehicle,
        geo-register the photographic data by associating each three dimensional vertex of the assembled point cloud data with a pixel of the photographic data based on the location of the transport vehicle,
        determine a color of the plant based on the photographic data of the plant,
        provide classification data of the plant comprising stem diameter, height, volume, and leaf density using the GPS coordinates of the assembled point cloud data,
        determine plant quality based on the color of the plant and one of the plant's stem diameter, height, volume, and leaf density, and
        provide instructions that control a fruit tree sprayer to spray the plant, wherein the instructions control when the fruit tree sprayer sprays, how long the fruit tree sprayer sprays, and what chemicals the fruit tree sprayer sprays on the plant based on the quality of the plant.

12. The plant analyzer of claim 11, further comprising a thermal video camera configured to collect thermal data and further wherein the quality of the plant is based on the thermal data.

13. The plant analyzer of claim 11, wherein the server is further configured to receive data from a multispectral or hyperspectral sensor for gathering spectral data.

14. The plant analyzer of claim 11, wherein the processor is further configured to generate an annotated photograph of the plant.

15. The plant analyzer of claim 11, wherein the processor further comprises a user interface configured to display the point cloud data, the photographic data, and the quality of the plant.

16. The plant analyzer of claim 11, wherein the processor is further configured to predict fruit yield of the plant, the predicted fruit yield determined by identifying a number of fruits on the plant based on the assembled point cloud data and the plant color.

* * * * *